United States Patent [19]

Sali

[11] Patent Number: Plant 7,237

[45] Date of Patent: May 29, 1990

[54] APPLE TREE: "SALI VARIETY"

[76] Inventor: Kasper B. Sali, 2004 Birchfield Rd., Yakima, Wash. 98901

[21] Appl. No.: 295,935

[22] Filed: Jan. 11, 1989

[51] Int. Cl.[5] ..... A01H 5/00

[52] U.S. Cl. ..... Plt./35

[58] Field of Search ..... Plt./35, 34

[56] References Cited

U.S. PATENT DOCUMENTS

| | | | |
|---|---|---|---|
| P.P. 1,565 | 2/1957 | Bisbee | Plt. 35 |
| P.P. 1,822 | 3/1959 | Gilbert | Plt. 35 |
| P.P. 1,882 | 12/1959 | Simonian et al. | 47/62 |
| P.P. 1,916 | 2/1960 | Hutchinson | Plt. 35 |
| P.P. 3,485 | 2/1974 | Coke | Plt. 35 |
| P.P. 3,556 | 5/1974 | Ward | Plt. 35 |
| P.P. 3,578 | 6/1974 | Campbell | Plt. 35 |
| P.P. 4,839 | 4/1982 | Evans et al. | Plt. 35 |
| P.P. 5,569 | 10/1985 | Gonzalez | Plt. 35 |

*Primary Examiner*—James R. Feyrer

*Attorney, Agent, or Firm*—Christensen, O'Connor, Johnson & Kindness

[57] ABSTRACT

A new variety of Red Delicious apple tree originating as a sport of the Gilbert Cultivar (U.S. Plant Pat. No. 1,822, exhibiting a distinctively semi-spur growth form and purplish overmature fruit coloration, and advantageously exhibiting substantially earlier color formation, earlier fruit maturation, and better resistance to sunburn than the parent tree and other Red Delicious varieties.

5 Drawing Sheets

The subject plant is a new and distinct variety of Red Delicious apple tree that was discovered by Kasper B. Sali, originating as a sport of the Redspur TM (Gilbert Cultivar) variety (U.S. Plant Pat. No. 1,822) in his orchard on Duffield Road in Moxee, Wash. This new variety has been fruited through three successive generations in the discoverer's orchard by budding and grafting, and has also been asexually reproduced in the Van Well Nursery orchard at Wenatchee, Wash. Each successive generation has proved true to the original bud sport so as to establish the genetic stability of this new variety, for which the varietal name 'Sali' is proposed.

BOTANICAL DESCRIPTION

Figure 1:
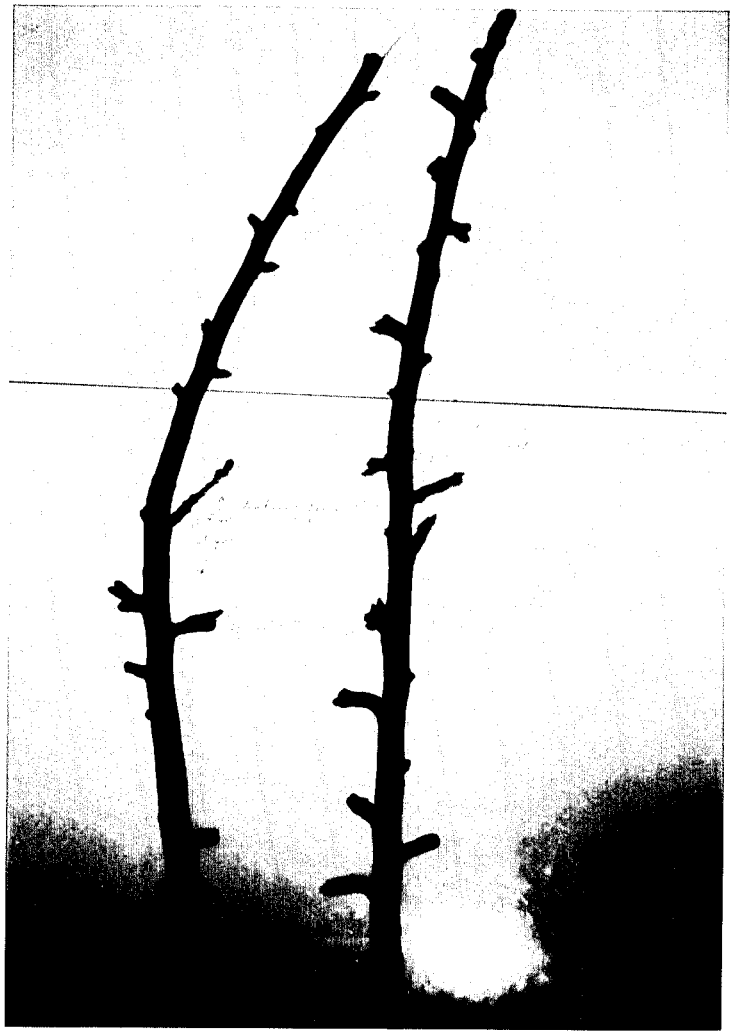
FIG. 1 shows spurs of 'Sali' (left) and the parent (right)

The following characteristics clearly distinguish this new variety from the parental stock:

Growth form: Whereas the parental trees characteristically exhibit a spur growth form, this new variety has a semi-spur growth form. For example, a representative limb from a fourteen-year-old tree of this new variety bears approximately 19 spurs per 30-inch length of wood, as compared to approximately 29 spurs on the same length of wood on the parental trees of comparable maturity grown in the same orchard. FIG. 1 shows representative limbs from this new variety (left) and the parental variety (right).

Early bloom Time: This new variety blooms two to four days earlier than other known Red Delicious apple trees, including Redspur TM, Red Chief TM (U.S. Plant Pat. No. 3,578), Scarlet Spur TM U.S. Plant Pat. No, 4,839), Topred TM (Hutchinson Cultivar, U.S. Plant Pat. No. 1,916), Rose Red TM (U.S. Plant Pat. No.

3,485), and Bisby strain (U.S. Plant Pat. No. 1,565) trees. I have compared the blooms of the subject trees in my orchard with Redspur TM, Topred TM, and Rose Red TM trees for five consecutive years, and each year this new variety has bloomed from two to four days earlier. For example, in 1986, full bloom on trees of this new variety was achieved on April 16, but the Redspur TM and other trees did not reach full bloom until April 20. In 1987, full bloom on this new variety occurred on April 17, which was four days earlier than for the Redspur TM and other trees.

Early fruit coloring: This new variety bears apples that begin coloring approximately thirteen days after full bloom, and full red blush color is achieved approximately forty days after full bloom, making this the earliest coloring Red Delicious tree that I have observed. Such early fruit coloring has been recorded for the past seven consecutive seasons on the original tree, and for the past two seasons on second and third generation trees in my orchard at Moxee, Wash.

Other early-coloring Red Delicious apple trees are known to include Scarlet Spur TM, Red Chief TM, Rico TM (U.S. Plant Pat. No. 5,569), and Early Red One (U.S. Plant Pat. No. 3,556). The Scarlet Spur TM and Red Chief TM varieties are spur trees and are thereby distinguished from this new variety, which exhibits a semi-spur growth form. Apples of the Rico TM tree color with a red strip on a yellowish ground color, in contrast to the blush coloration that distinguishes this new variety. Apples of the Early Red One TM tree also color with a stripe. In addition, the Early Red One TM tree is distinguished from this new variety by bearing leaves that are distinctively smaller, with light green, grayish underside coloration.

Sunburn: Due to the distinctively early, intense coloring factor, the apples of this new Red Delicious variety, as sampled from approximately 800 trees, exhibited very low levels sunburn from the extreme sunlight conditions of the 1987 growing season. That is, apples of the subject trees advantageously retained their red-coloration and crisp texture.

Early fruit maturity: At approximately 125-135 from full bloom the fruit of this new variety is matured, i.e., the apples have brown seeds, white flesh, and, most importantly, a soluble solids content of 10.5% or higher. This advantageous characteristic is demonstrated by the following tabulation of soluble solids content data (%), sampled at periodic percent intervals (month-day) during six consecutive growing seasons, from apples grown in my orchard on trees of this new variety ("Sali") and the early-coloring Red Chief TM variety.

| | SALI | | | | RED CHIEF | | | |
|---|---|---|---|---|---|---|---|---|
| | 8-18 | 8-25 | 9-1 | 9-8 | 8-18 | 8-25 | 9-1 | 9-8 |
| 1982 | 9.6 | 10.4 | 10.2 | 10.8 | 8.8 | 10.0 | 10.0 | 9.8 |
| 1983 | — | — | — | 11.0 | — | — | — | 10.8 |
| 1984 | — | — | 11.5 | 11.9 | — | — | 11.9 | 11.7 |
| 1985 | — | 11.7 | 13.1 | 12.6 | — | 9.3 | 9.9 | 10.9 |
| 1986 | 10.6 | 11.0 | 11.2 | 11.3 | 9.8 | 9.2 | 11.1 | 10.6 |
| 1987 | — | 11.0 | 11.2 | — | — | — | — | — |

Figure 2:
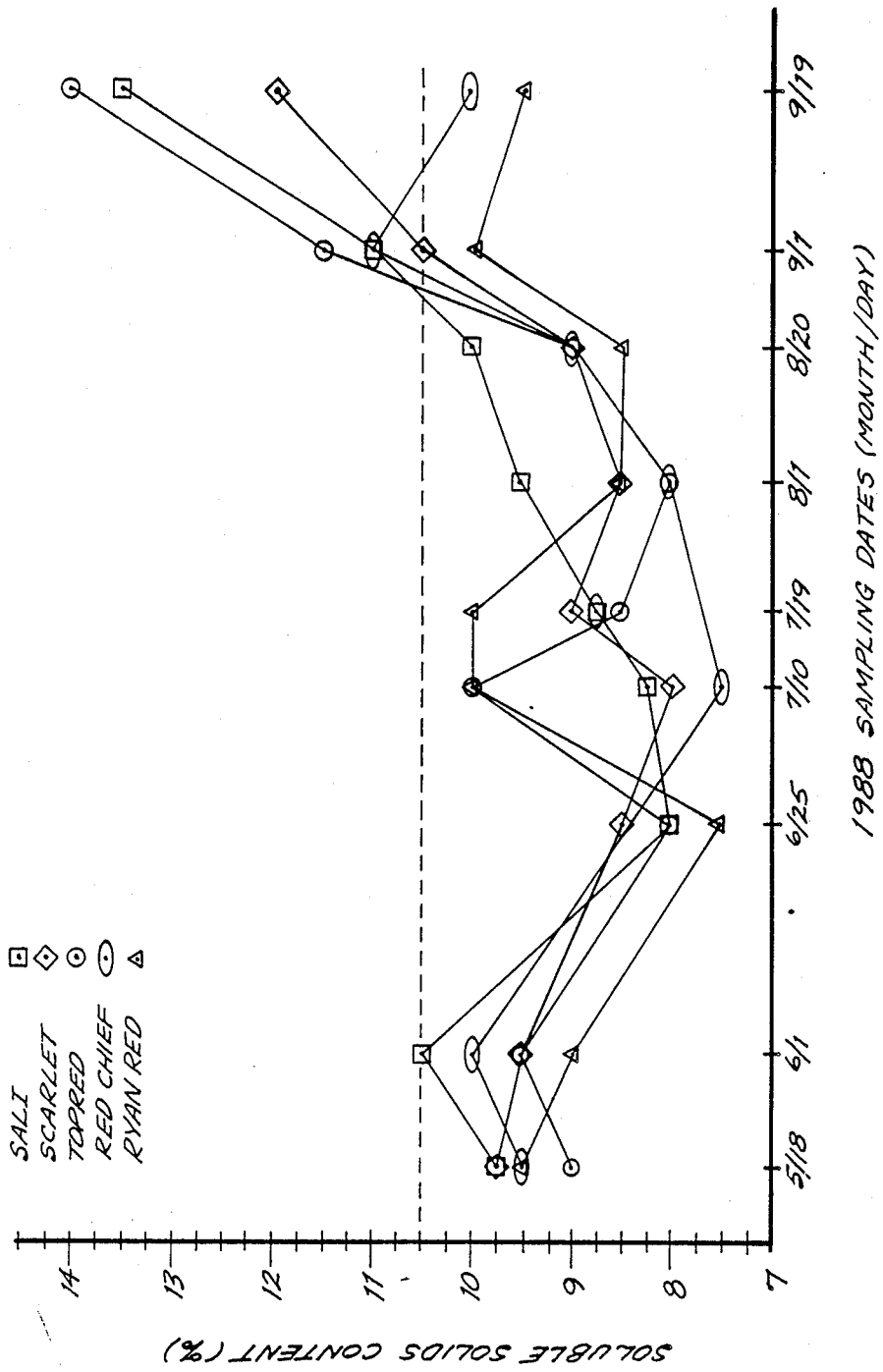
FIG. 2 shows comparative, progressive changes in soluble solids content of 'Sali' and related varieties.

Referring now to FIG. 2, comparative data is presented from the 1988 growing season. Soluble solids content of representative apples (%, plotted on the y-axis) was sampled periodically percent throughout the growing season (month-day), on the x-axis) for trees of this new variety as compared with Scarlet Spur TM, Topred TM, Ryanred Spur TM, and Red Chief TM trees, all grown in the same orchard.

Figure 3A:
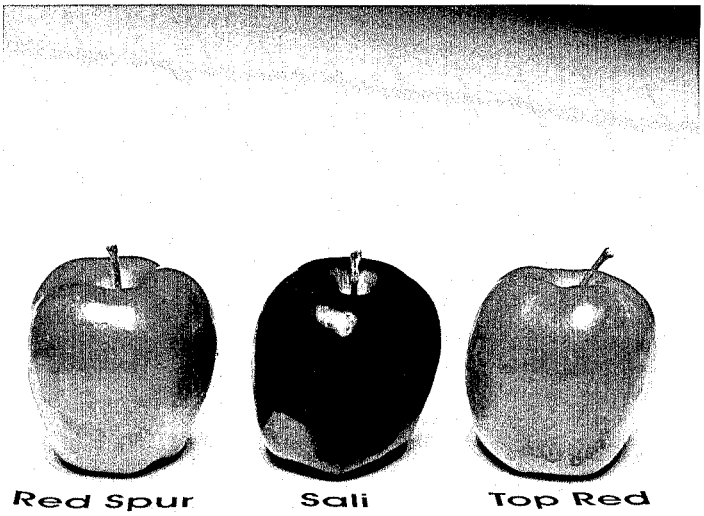
FIGS. 3A depicts perspective and 3B shows cross-sectioned apples of (from left to right) 'Red Spur', 'Sali' and 'Top Red'.
Figure 3B:
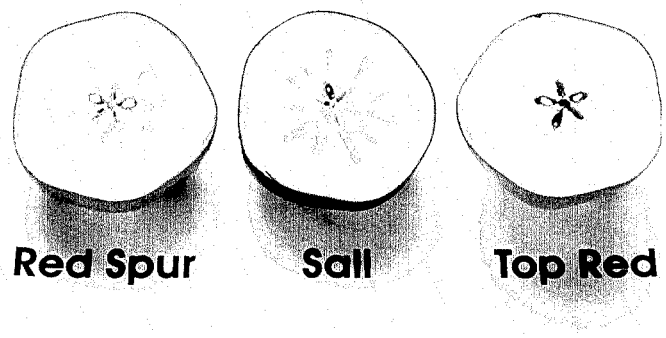

Purple overmature coloration: If picking is delayed past the mature stage, the fruit of this new variety develops a distinctly purple coloration, somewhat like the apples of the Early Red One TM tree.FIGS. 3A and 3B show the overmature Sali variety apple, as compared with Redspur TM and Topred TM apples. Some purplish apples of the subject variety develop red veins in the fruit flesh.

The following description of this new variety of Red Delicious apple tree characterizes both the original and the asexually propagated trees.

TREE

Figure 4:
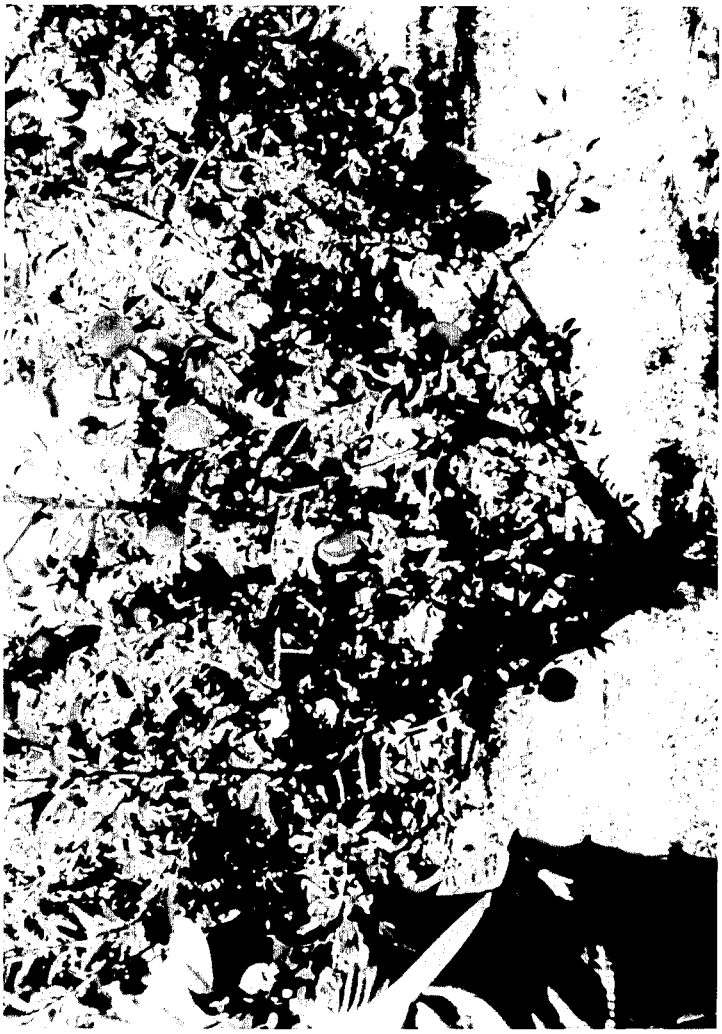
FIG. 4 shows tree shape.

Growth form: The tree is vigorous with an upright growth form (FIG. 4). Vase-formed in shape, the tree is of medium to tall height and exhibits a semi-spur growth form. The trunk tends to be stalky, with smooth bark. The branches tend to be slender, with smooth, gray bark. Tree lenticles are numerous and large in size. The branchlets tend to be slender, medium-jointed, and gray. The branching angle of the branchlets is average, and internodes are of medium length.

Leaf: Leaves are medium in size, narrow, and taper-pointed. The leaves are of medium thickness, medium green in color (including the undersides), and rugose. Leaf buds are small to medium in overall size, and long and slender in shape. Leaf margins are coarsely serrated, as in the parental variety.

Flowers: As mentioned above, this new variety is a distinctly early bloomer. The white blossoms are medium in size with petals of average size and shape. The flowers are self-sterile. The distribution of blossoms on the tree is average, with many flower clusters.

This new variety is a hearty, productive, and regular bearer. Its susceptibility to insects and diseases is similar to other Red Delicious trees.

FRUIT

Shape: The symmetrical apples are of medium size, typically three to three-and-one-fourth inches in length, about three inches in width, and of roundish to conical shape. The apples hang well on short, thick stems. The cavity at the stem end is smooth and of medium depth and width. The calyx is closed and of medium size.

Skin: Fruit skin is of medium thickness, smooth, waxen and glossy.

Figure 5:
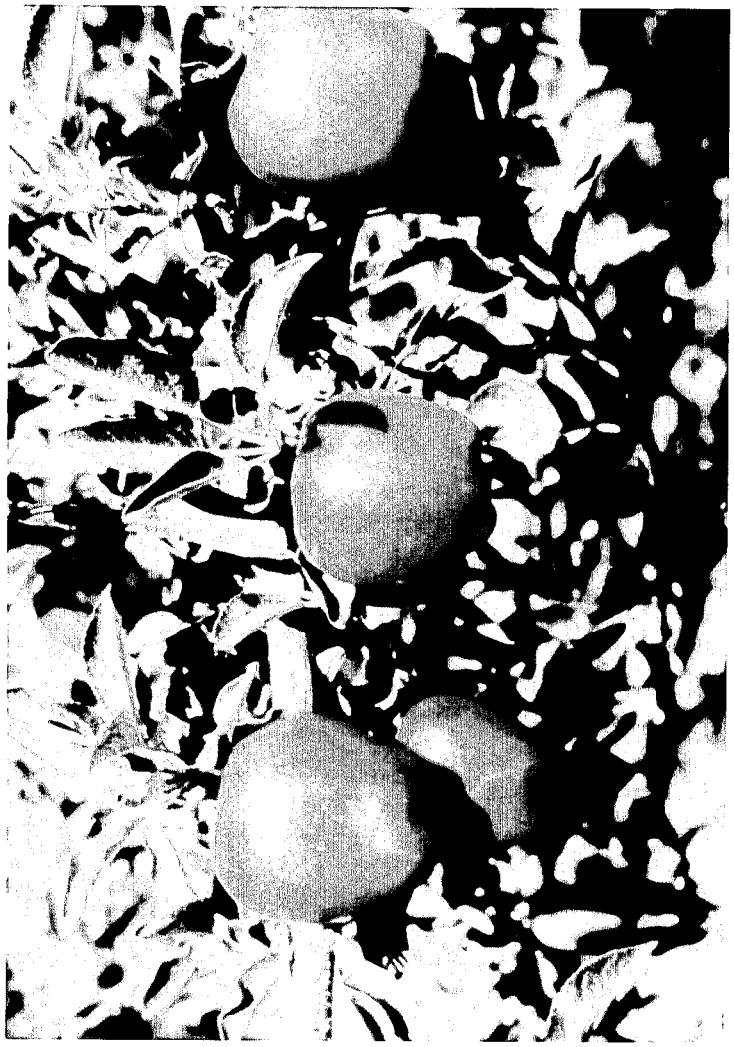
FIG. 5 depicts a stem bearing mature fruit of 'Sali'.

Skin color: The red overcolor develops by blush color formation. Ground color is an attractive yellow with overcolor that initiates very early as splashes (not stripes). As mentioned above, color development is distinctly early for a Red Delicious variety. At maturity, the apple is a solid red color (FIG. 5). The mature apple coloration, as identified using Ridgeway's Color Standards and Nomenclature (1912), is Violet Carmine (Plate XII).

Flesh: The flesh is greenish white, red streaked, firm, and crisp. The juicy, sweet flesh is of best quality.

Seeds: The medium-sized core has five seed cells, with two seeds per cell. At maturity, the seeds are colored brown, have acute points, and are of average size, typically about 5/16 of an inch in length and 3/16 of an inch in breadth.

Use: The fruit is a commercially marketable dessert apple of best quality.

I claim:

1. A new and distinct variety of apple tree substantially as shown and described.

* * * * *